United States Patent
Bae et al.

(10) Patent No.: US 7,551,364 B2
(45) Date of Patent: Jun. 23, 2009

(54) INSULATING SOLUTION FOR LIQUID LENS WITH HIGH RELIABILITY AND LIQUID LENS USING THE SAME

(75) Inventors: Jae Young Bae, Gyunggi-Do (KR); Jong Yun Kim, Gyunggi-Do (KR); Ha Yong Jung, Gyunggi-Do (KR); Sung Soo Park, Gyunggi-Do (KR)

(73) Assignee: Samsung Electro-Mechanics Co., Ltd., Suwon (KR)

( * ) Notice: Subject to any disclaimer, the term of this patent is extended or adjusted under 35 U.S.C. 154(b) by 304 days.

(21) Appl. No.: 11/706,204

(22) Filed: Feb. 15, 2007

(65) Prior Publication Data

US 2007/0199454 A1 Aug. 30, 2007

(30) Foreign Application Priority Data

Feb. 15, 2006 (KR) .................. 10-2006-0014535

(51) Int. Cl.
 *G02B 1/06* (2006.01)
(52) U.S. Cl. ...................... 359/665; 359/666
(58) Field of Classification Search ................ 359/665, 359/666
 See application file for complete search history.

(56) References Cited

U.S. PATENT DOCUMENTS

| 4,006,226 A | 2/1977 | Bennett |
| 7,327,524 B2 * | 2/2008 | Renders et al. ............. 359/666 |

FOREIGN PATENT DOCUMENTS

GB 971598 9/1964

OTHER PUBLICATIONS

X. Wang, "Determination of Enantiomeric Purity of Alcohols Using Achiral Diphenyldichlorosilane", Tetrahedron Letters, vol. 32, No. 30, 1991, pp. 3651-3654.

Xuebao Wang, "Determination of Enatiomeric Purity of Alcohols Using Achiral Diphenyldichlorosilane," Tetrahedron Letters, vol. 32, No. 30, published Dec. 31, 1991 (previously cited).

Chinese Office Action issued Mar. 6, 2009 in corresponding Chinese Patent Application 200710079352.0.

* cited by examiner

*Primary Examiner*—William C Choi

(57) ABSTRACT

Silicone oil used for an insulating solution for a liquid lens is disclosed which satisfies all of the requirements, i.e., density, viscosity, surface tension and refractive index, required as an insulating liquid for a liquid lens.

The silicone oil includes at least one selected from compounds represented by Formulas 1 to 3 below:

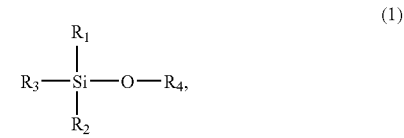

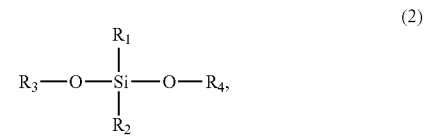

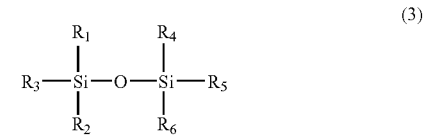

wherein $R_1$ to $R_6$ are same or different each other; and are independently selected from the group consisting of phenyl being replaced by alkyl or halo in ortho, meta or para position, silanol, alkyl and alkoxy each having a molecular weight of 200 or less.

20 Claims, 1 Drawing Sheet

INSULATING SOLUTION FOR LIQUID LENS WITH HIGH RELIABILITY AND LIQUID LENS USING THE SAME

CLAIM OF PRIORITY

This application claims the benefit of Korean Patent Application No. 2006-14535 filed on Feb. 15, 2006, in the Korean Intellectual Property Office, the disclosure of which is incorporated herein by reference.

BACKGROUND OF THE INVENTION

1. Field of the Invention

The present invention relates to a liquid for a liquid lens. More specifically, the present invention relates to silicone oil having a specific structure used for an insulating solution for a liquid lens and an insulating solution comprising the silicone oil.

2. Description of the Related Art

In recent years, rapid growth in mobile communication apparatus and computer technology as well as consumers' diverse needs have brought about fierce international competition for technology improvements to realize lenses with auto focus (A/F) and optical zoom. As general methods to obtain lenses with auto focus (A/F) and optical zoom, there may be used mechanical movement of a lens, variation in curvature of a lens and changes in physical properties of a lens. In the case of general multi-focus optical lenses commercialized in digital cameras, etc., the distance between a plurality of lenses having a predetermined refractive index must be mechanically varied, thus involving disadvantageously high costs and taking up much space. Accordingly, most cameras in notebooks and cellular phones having strict restrictions on volume are being provided with lenses incapable of automatic focusing.

Liquid lens is a new technology that realizes auto focus (A/F) and optical zoom functions by variation in curvature thereof based on the electrowetting phenomenon. Liquid lenses are usable as a micro-optical zoom lens for a variety of cameras and mobile communication apparatus, etc., owing to reduced consumption power and minimized volume. In addition, liquid lenses are widely utilized in a variety of applications, including computer components and optical devices.

An insulating solution must have chemical stability and be stably operated in operational and conservative temperature ranges. The insulating solution must have the similar density and viscosity to those of a conductive electrolyte solution to ensure an easy operation upon application of a voltage and maintain an interface between the insulating solution and the electrolyte solution.

As the difference in surface tension between the two solutions increases and the difference in refractive index between the two solutions decreases, stability at the interface between the solutions and device performance tend to improve.

Although a number of patent applications associated with conventional liquid lenses describe a use of a silicone oil as an insulating solution for a liquid lens, they fail to specifically disclose the insulating solution suitable for use in a liquid lens. Accordingly, general silicone oils are currently being used as an insulating solution for a liquid lens.

However, general silicone oils do not satisfy the requirements, i.e., density, refractive index and viscosity conditions, for an insulating solution for a liquid lens. Accordingly, to satisfy these requirements, a mixture of an excess organic additive and such a silicone oil is being currently used.

As a result of repeated eager studies, the inventors found that when the organic additive is used in an excessive amount, it has a strong tendency to adhere to the inner surface of a hydrophilic liquid lens due to its hydrophilicity, thus having a variety of bad effects on operation of the liquid lens, e.g., insufficient operation. Accordingly, the inventors confirmed that the organic additive must be used in a minimum amount.

SUMMARY OF THE INVENTION

The present invention has been made to solve the foregoing problems of the prior art and therefore it is one aspect of the present invention to provide a silicone oil having a specific structure suitable for use as an insulating solution for a liquid lens.

It is another aspect of the present invention to provide an insulating solution for a liquid lens that stably operates in operational and conservative temperature ranges and has substantially the same density and viscosity as those of an electrolyte solution although an organic additive is used in a small amount.

It is another aspect of the present invention to provide an insulating composition suitable for use as an insulating solution for a liquid lens wherein the insulating composition contains the silicone oil and a minimum amount of an organic additive, thereby minimizing bad effects on operation of a liquid lens associated with an excessive organic additive.

It is yet another aspect of the invention to provide a liquid lens module comprising an insulating solution as the insulating composition and an electrolyte solution.

In accordance with one aspect of the present invention, there is provided a silicone oil used as an insulating solution for a liquid lens, the silicone oil comprising at least one selected from compounds represented by Formulas 1 to 3 below:

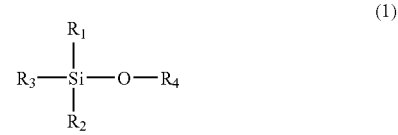

wherein $R_1$ to $R_4$ are same or different each other; and are independently selected from the group consisting of phenyl being replaced by alkyl or halo in ortho, meta or para position, silanol, alkyl and alkoxy each having a molecular weight of 200 or less;

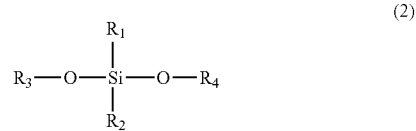

wherein $R_1$ to $R_4$ are as defined in Formula 1; and

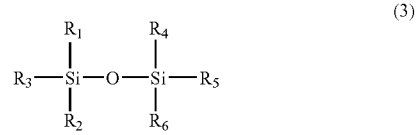

wherein $R_1$ to $R_6$ are as defined in $R_1$ to $R_4$ of Formula 1.

In accordance with another aspect of the present invention, there is provided an insulating composition containing 85 to 90% by weight of the silicone oil and 10 to 15% by weight of an organic additive.

In accordance with another aspect of the present invention, there is provided an insulating solution containing the silicone oil and an organic additive.

In accordance with yet another aspect of the present invention, there is provided a liquid lens module comprising: a transparent cover; a case for accommodating an insulating solution and an electrolyte solution; a pair of electrodes for supplying electricity to the electrolyte solution; and an insulating film for covering one of the electrodes in contact with the electrolyte solution.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
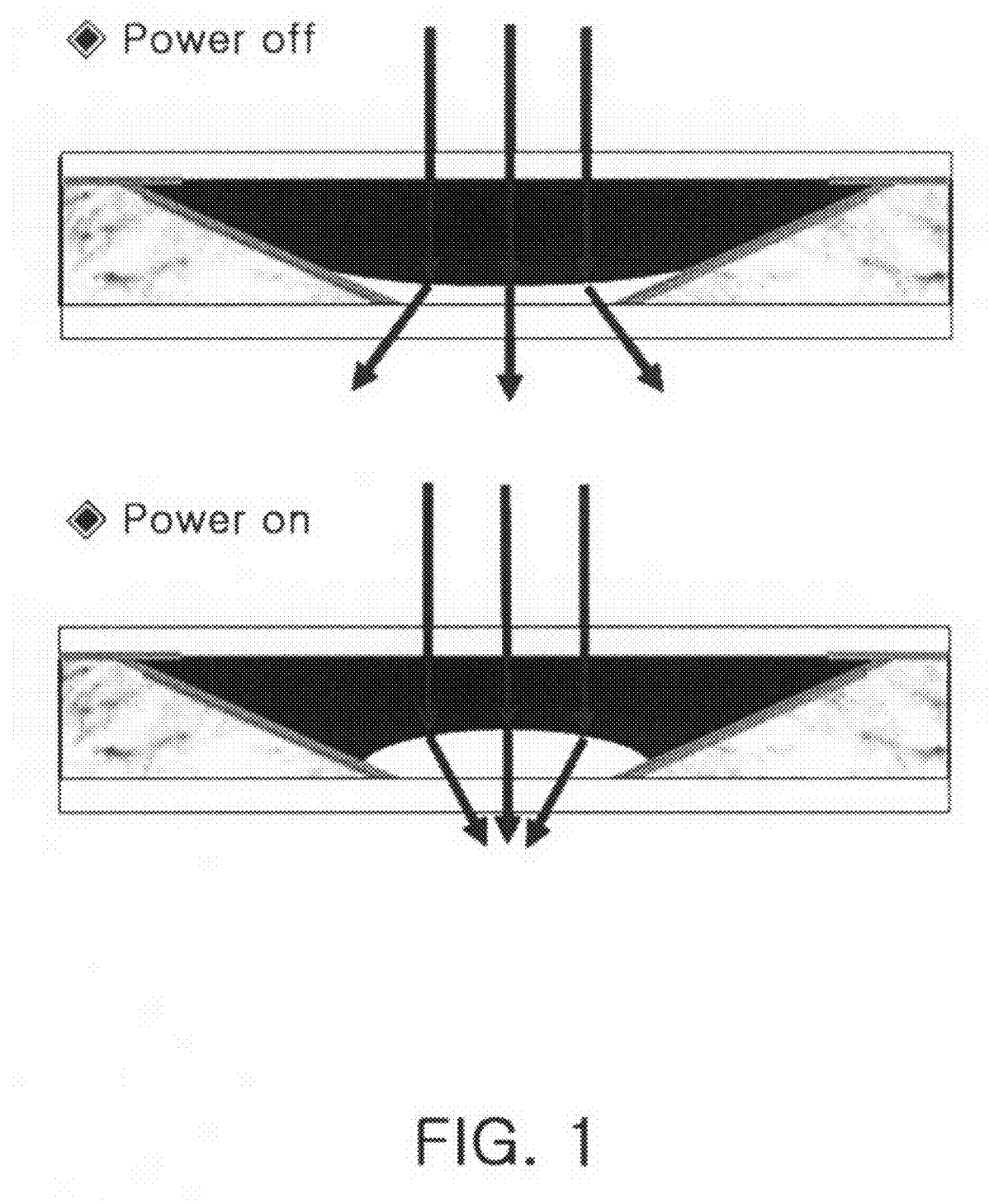
FIG. 1 is a schematic diagram illustrating operational characteristics of a liquid for a liquid lens using an insulating solution comprising the silicone oil represented by Formula 4 according to the present invention.

The present invention will now be described in greater detail.

The inventors found that a silicone oil is usable for an insulating solution for a liquid lens by adjusting the density, viscosity and refractive index of a liquid for a liquid lens while taking into consideration correlation between the insulating solution and an electrolyte solution. To systematically establish the basic physical properties of the silicone oil and apply them to the insulating solution, the inventors have compared theoretical values of the physical properties calculated with the introduction of molecular computational chemistry with actual measured values thereof, thereby realizing optimization of a silicone oil structure suitable for use in an insulating solution for a liquid lens.

A silicone oil used as an insulating solution for a liquid lens according to the present invention may comprise at least one selected from compounds represented by Formulas 1 to 3 below:

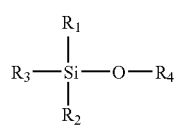
(1)

wherein $R_1$ to $R_4$ are same or different each other; and are independently selected from the group consisting of phenyl being replaced by alkyl or halo in ortho, meta or para position, silanol, alkyl and alkoxy each having a molecular weight of 200 or less;

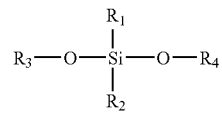
(2)

wherein $R_1$ to $R_4$ are as defined in Formula 1; and

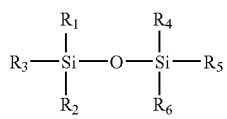
(3)

wherein $R_1$ to $R_6$ are as defined in $R_1$ to $R_4$ of Formula 1.

The silicone oil that may be used as an insulating solution for a liquid lens is preferably the compound of Formula 2.

$R_1$ and $R_2$ in Formula 2 are same or different each other and are independently selected from the group consisting of phenyl being replaced by alkyl or halo in ortho, meta or para position. $R_3$ and $R_4$ in Formula 2 are same or different each other and are at least one selected from the group consisting of silanol, alkyl and alkoxy each having a molecular weight of 200 or less.

Each of the silicone oils of Formulas 1 to 3 has a density of 0.945 to 0.995 g/cm$^3$, a viscosity of 8.0 to 21.5 mPa·s and a refractive index of 1.50 to 1.51 $n_D^{20}$.

Examples of preferred silicone oils may include the following compounds represented by Formulas 4 to 6 which are derived from the compound of Formula 2:

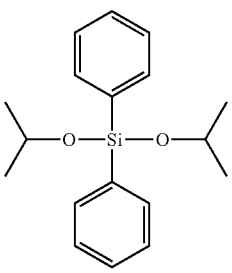
(4)

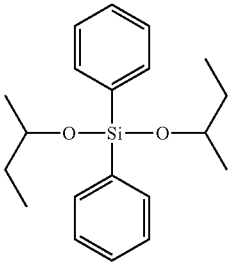
(5)

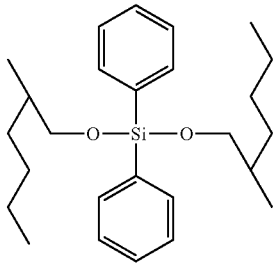
(6)

More preferred are the compounds of Formulas 4 and 5. Most preferred is the compound of Formula 4.

The density, viscosity, surface tension, and refractive index are measured for each compound of Formulas 4 to 6. The results are shown in Table 1.

TABLE 1

| Silicone oil | Density (g/cm$^3$) | Viscosity (mPa·s) | Surface tension (mN/m) | Refractive index ($n_D^{20}$) |
|---|---|---|---|---|
| Compound (4) $R_1, R_2$ = phenyl $R_3, R_4$ = isopropyl | 0.992 | 8.04 | 29.0 | 1.508 |
| Compound (5) $R_1, R_2$ = phenyl $R_3, R_4$ = butyl | 0.973 | 12.5 | 25.3 | 1.505 |
| Compound (6) $R_1, R_2$ = phenyl $R_3, R_4$ = heptyl | 0.948 | 21.1 | 29.5 | 1.501 |

Preferably, an insulating solution for a liquid lens has a density of 1.0 g/cm$^3$ or more, a viscosity of 10 mPa·s or less and a refractive index of 1.5 $n_D^{20}$ or more. The gap in physical properties between the desired insulating solution and the silicone oils of the present invention can be adjusted by using a small amount of an organic additive, thereby realizing optimization of an insulating solution for a liquid lens.

As can be seen from Table 1, as molecular weights of $R_3$ and $R_4$ increase, the density of a silicone oil tends to decrease and the viscosity thereof tends to increase. As the silicone oil has a lower density and a higher viscosity than those required for a liquid lens, the content of the organic additive must be increased to suitably use the silicone oil as an insulating solution for a liquid lens. Accordingly, it can be seen that $R_3$ and $R_4$ having a molecular weight of 90 or less be more preferred.

Examples of the organic additive that may be used to adjust physical properties of an insulating solution for a liquid lens include dibromohexane, dichlorobenzene, 1-bromo-3-chlorobenzene, 1-bromo-2-chlorobenzene, bromobenzene, tetrabromohexane, 1,10-dichlorodecane and 1-chloronaphthalene.

The use of the organic additive enables the density of the silicone oil to be elevated, or the viscosity thereof to be lowered. The adjustment of the density and viscosity by the organic additive imparts physical properties required for use in a liquid lens to the silicone oil.

More specifically, the use of the organic additive imparts an increased density of 1 g/cm$^3$ or more to the compound of Formula 4, and an increased density and a reduced viscosity to the compound of Formula 5.

On the other hand, the use of general silicone oils involves an excessive organic additive (i.e., about 30 wt %) for adjustment of the physical properties, e.g., density, viscosity, surface tension and/or refractive index, required as an insulating solution for a liquid lens. When the organic additive is used in an excessive amount, it has a strong tendency to adhere to the inner surface of a hydrophilic liquid lens due to its hydrophilicity, thus affecting adversely on operational performance of the liquid lens and stabilization at the interface thereof. Accordingly, most preferred is to avoid the use of any organic additive. But, it is inevitable to use the organic additive, because the silicone oils have no physical properties required as an insulating solution for a liquid lens.

The organic additive must be used as low as possible. The silicone oils having a specific structure that may used as an insulating solution according to the present invention contribute to minimizing the content of the organic additive.

The insulating composition contains 85 to 90% by weight of a silicone oil, which may comprise at least one compound selected from compounds of Formulas 1 to 3, and 10 to 15% by weight of an organic additive. The content of the organic additive lower than 10 wt % makes it difficult to impart the desired density and viscosity to the silicone oil. Meanwhile, the content of the organic additive higher than 15 wt % disadvantageously causes an excessive increase in density and viscosity of the silicone oil.

In silicone oils of Formulas 1 to 3, $R_1$ to $R_6$ are same or different each other, and are independently selected from the group consisting of phenyl being replaced by alkyl or halo in ortho, meta or para position, silanol, alkyl and alkoxy each having a molecular weight of 200 or less.

More preferably, the compound of Formula 2 may be used as a silicone oil. $R_1$ and $R_2$ in Formula 2 are same or different each other, and are independently selected from the group consisting of phenyl being replaced by alkyl or halo in ortho, meta or para position. $R_3$ and $R_4$ in Formula 2 are same or different each other, and are at least one selected from the group consisting of silanol, alkyl and alkoxy each having a molecular weight of 200 or less.

Examples of preferred silicone oils may include the compounds of Formulas 4 to 6. More preferred are the compounds of Formulas 4 and 5. Most preferred is the compound of Formula 4.

An insulating solution for a liquid lens can be prepared from the silicone oil according to the present invention. The silicone oil may contain an organic additive. The prepared insulating solution for a liquid lens has a density of 1.0 g/cm$^3$ or more equal to that of the electrolyte solution, a refractive index of 1.5 $n_D^{20}$ or more greater than that of the electrolyte solution, a viscosity of 10.0 mPa·s or less substantially equal to that of the electrolyte solution in which the difference in viscosity between the two solutions is within 0.5 mPa·s, and a surface tension of 30 mN/m or less. Accordingly, the insulating solution satisfies all of the requirements.

Although the insulating solution of the present invention contains a small amount of the organic additive, as compared to conventional silicone oils, it can efficiently obtain the desired physical properties, thereby solving an unstable operation associated with the organic additive.

The insulating solution of the present invention can be utilized in a liquid for a liquid lens. The liquid for a liquid lens comprises the insulating solution and a conductive electrolyte solution. An interface is formed between the two solutions. The organic additive used in a reduced amount contributes to an improvement in stability of the interface, thus stably maintaining the interface upon operating the liquid lens.

Furthermore, the present invention provides a liquid lens module using the liquid for a liquid lens. The liquid lens module comprises a transparent cover, a case for accommodating an electrolyte solution and an insulating solution, a pair of electrodes for supplying electricity to the electrolyte solution, and an insulating film for covering one of the electrodes in contact with the electrolyte solution. The insulting solution used herein may be the same as used in the present invention.

EXAMPLES

Hereinafter, the present invention will be explained in more detail with reference to the following examples. However, these examples are given for the purpose of illustration and are not intended to limit the present invention.

Each silicone oil of Formulas 4 and 5, and a general silicone oil were measured for the density, refractive index, viscosity and surface tension. Whether or not the silicone oils satisfy the requirements as an insulating solution are evaluated, while taking into consideration correlation between the insulating solution of each silicone oil and a conductive electrolyte solution.

The density, the refractive index, the viscosity and the surface tension were measured by using a pycnometer, an ABBE refractometer, a single cylinder rotational viscometer, and a KRUSS k10ST, respectively.

The silicone oil of Formula 4 used herein was compound wherein $R_1$ and $R_2$ are phenyl, and $R_3$ and $R_4$ are isopropyl. The silicone oil of Formula 5 used herein was compound wherein $R_1$ and $R_2$ are phenyl, and $R_3$ and $R_4$ are butyl. The general silicone oil used herein was KF56® (available from Shin-Etsu Chemical Co., Ltd.). The electrolyte solution used herein was SEL02.

In the case where the silicone oil has a density of 1 g/cm$^3$, a refractive index of 1.5 $n_D^{20}$ or more, a viscosity of 10.0 mPa·s or less, and a surface tension of 30 mN/m or less, the silicone oil was evaluated to be suitable for use as an insulating solution for a liquid lens. Considering correlation between the two solutions, the insulating solution has the same density as the electrolyte solution, a refractive index greater than that of the electrolyte solution, and a viscosity substantially equal to that of the electrolyte solution wherein the difference in viscosity between the two solutions is within 0.5 mPa·s. The measurement results for the samples are shown in Table 2.

TABLE 2

| Silicone oil | Density (g/cm$^3$) | Refractive index ($n_D^{20}$) | Viscosity (mPa · s) | Surface tension (mN/m) | |
|---|---|---|---|---|---|
| Compound (4) $R_1, R_2$ = phenyl $R_3, R_4$ = isopropyl | 0.991 | 1.508 | 8.04 | 29.0 | Refractive index, viscosity: good |
| Compound (5) $R_1, R_2$ = phenyl $R_3, R_4$ = butyl | 0.973 | 1.505 | 12.5 | 25.3 | Refractive index, viscosity: good |
| KF56 | 0.995 | 1.497 | 14.6 | 26.5 | Refractive index: poor |
| SEL02 | 1.092 | 1.402 | 8.2 | 47.7 | — |

It can be seen from Table 2, the silicone oil of the present invention had substantially the same values of physical properties, e.g., density, viscosity, surface tension and/or refractive index, as those required as an element of an insulating solution for a liquid lens. Although an organic additive is used in a small amount, the insulating solution satisfies the requirements. In addition, the insulating solution satisfies the conditions essential for correlation with the electrolyte solution.

On the other hand, although KF56 satisfied the requirements for density, viscosity and surface tension, it was evaluated to be unsuitable for use as an insulating solution due to its insufficient refractive index. The use of the organic additive hardly affects on the refractive index. Accordingly, it is inevitable to use an excessive organic additive.

FIG. 1 illustrates operational characteristics of a liquid for a liquid lens prepared by using the compound of Formula 4 according to the present invention as an insulating solution, and SEL02 as an electrolyte solution. As shown in FIG. 1, the liquid for a liquid lens exhibits a stable and superior operational performance.

The use of the silicone oil of the present invention as an insulating solution for a liquid lens enables a reduction in an amount of an organic additive contained in the insulating composition, when compared to conventional insulating compositions. In addition, although the organic additive is used in a small amount, the insulating solution satisfies the requirements, thereby solving an unstable operation associated with an excessive organic additive.

While the present invention has been shown and described in connection with the exemplary embodiments, it will be apparent to those skilled in the art that modifications and variations can be made without departing from the spirit and scope of the invention as defined by the appended claims.

The invention claimed is:

1. A liquid lens comprising a silicone oil used for an insulating solution for said liquid lens, the silicone oil comprising at least one selected from compounds represented by Formulas 1 to 3 below:

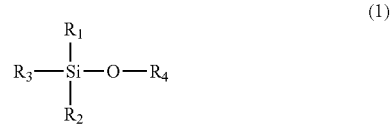

wherein $R_1$ to $R_4$ are same or different each other; and are independently selected from the group consisting of phenyl being replaced by alkyl or halo in ortho, meta or para position, silanol, alkyl and alkoxy each having a molecular weight of 200 or less;

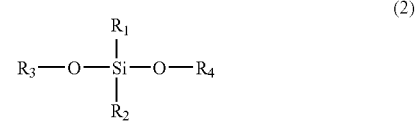

wherein $R_1$ to $R_4$ are as defined in Formula 1; and

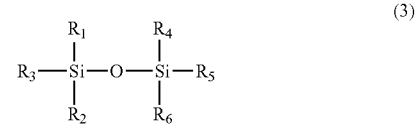

wherein $R_1$ to $R_6$ are as defined in $R_1$ to $R_4$ of Formula 1.

2. The silicone oil according to claim 1, wherein the liquid lens is the compound of Formula 2.

3. The liquid lens according to claim 2, wherein $R_1$ and $R_2$ in Formula 2 are independently phenyl being replaced by alkyl or halo in ortho, meta or para position, and $R_3$ and $R_4$ in Formula 2 are independently silanol, alkyl or alkoxy each having a molecular weight of 200 or less.

4. The liquid lens according to claim 3, wherein $R_3$ and $R_4$ in Formula 2 are independently silanol, alkyl or alkoxy each group having a molecular weight of 90 or less.

5. The liquid lens according to claim 3, wherein the compound is selected from compounds represented by Formulas 4 to 6 below:

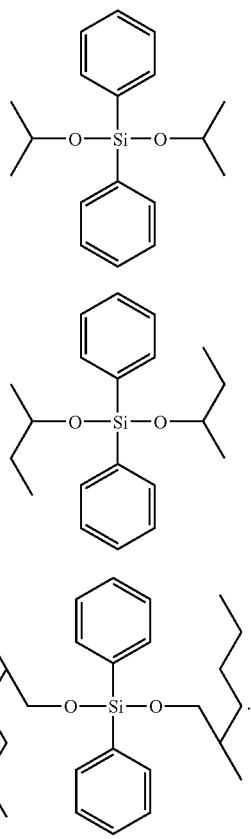

6. The liquid lens according to claim 1, wherein the silicone oil has a density of 0.945 to 0.995 g/cm$^3$, a refractive index of 1.50 to 1.51 $n_D^{20}$, and a viscosity of 8 to 21.5 mPa·s.

7. A liquid lens comprising an insulating composition for said liquid lens containing 85 to 90% by weight of a silicone oil and 10 to 15% by weight of an organic additive, wherein the silicone oil comprises at least one selected from compounds represented by Formulas 1 to 3 below:

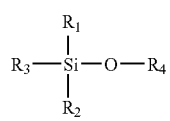

wherein $R_1$ to $R_4$ are same or different each other; and are independently selected from the group consisting of phenyl being replaced by alkyl or halo in ortho, meta or para position, silanol, alkyl and alkoxy each having a molecular weight of 200 or less;

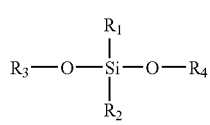

wherein $R_1$ to $R_4$ are as defined in Formula 1; and

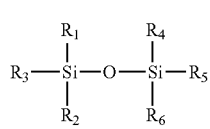

wherein $R_1$ to $R_6$ are as defined in $R_1$ to $R_4$ of Formula 1.

8. The liquid lens according to claim 7, wherein the silicone oil is the compound of Formula 2, wherein $R_1$ and $R_2$ are independently phenyl being replaced by alkyl or halo in ortho, meta or para position, and $R_3$ and $R_4$ are independently silanol, alkyl or alkoxy each having a molecular weight of 200 or less.

9. The liquid lens according to claim 8, wherein the silicone oil comprises at least one selected from compounds represented by Formulas 4 to 6 below:

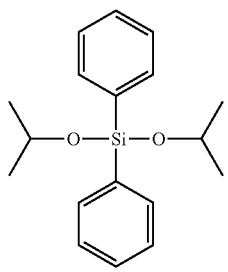

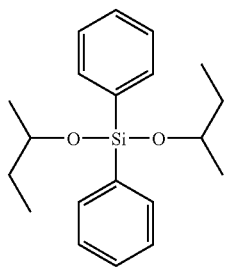

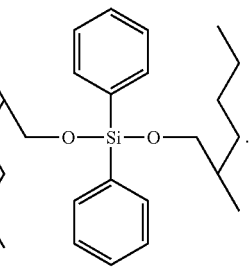

10. A liquid lens module comprising:
a transparent cover;
a case for accommodating an electrolyte solution and an insulating solution;
a pair of electrodes for supplying electricity to the electrolyte solution; and
an insulating film for covering one of the electrodes in contact with the electrolyte solution,
wherein the insulating solution is the insulating composition according to claim 9.

11. A liquid lens module comprising:
a transparent cover;
a case for accommodating an electrolyte solution and an insulating solution;
a pair of electrodes for supplying electricity to the electrolyte solution; and
an insulating film for covering one of the electrodes in contact with the electrolyte solution,
wherein the insulating solution is the insulating composition according to claim 8.

12. The liquid lens according to claim 7, wherein the organic additive comprises at least one selected from the group consisting of dibromohexane, dichlorobenzene, 1-bromo-3-chlorobenzene, 1-bromo-2-chlorobenzene, bromobenzene, tetrabromohexane, 1, 10-dichlorodecane and 1-chloronaphthalene.

13. A liquid lens module comprising:
a transparent cover;
a case for accommodating an electrolyte solution and an insulating solution;
a pair of electrodes for supplying electricity to the electrolyte solution; and
an insulating film for covering one of the electrodes in contact with the electrolyte solution,
wherein the insulating solution is the insulating composition according to claim 10.

14. A liquid lens module comprising:
a transparent cover;
a case for accommodating an electrolyte solution and an insulating solution;
a pair of electrodes for supplying electricity to the electrolyte solution; and
an insulating film for covering one of the electrodes in contact with the electrolyte solution,
wherein the insulating solution is the insulating composition according to claim 7.

15. A liquid lens comprising an insulating composition for said liquid lens containing a silicone oil and an organic additive,
wherein the silicone oil comprises at least one selected from compounds represented by Formulas 1 to 3 below:

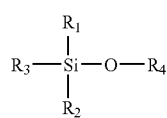
(1)

wherein $R_1$ to $R_4$ are same or different each other; and are independently selected from the group consisting of phenyl being replaced by alkyl or halo in ortho, meta or para position, silanol, alkyl and alkoxy each having a molecular weight of 200 or less;

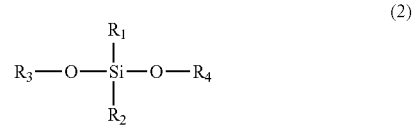
(2)

wherein $R_1$ to $R_4$ are as defined in Formula 1; and

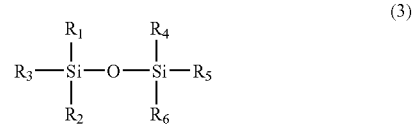
(3)

wherein $R_1$ to $R_6$ are as defined in $R_1$ to $R_4$ of Formula 1.

16. The liquid lens according to claim 15, wherein the silicone oil comprises at least one selected from compounds represented by Formulas 4 to 6 below:

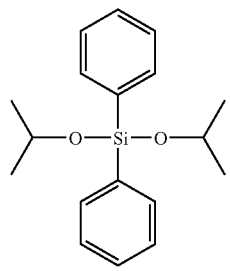
(4)

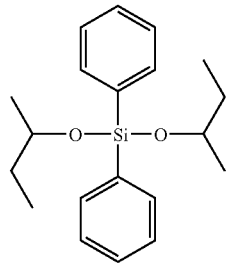
(5)

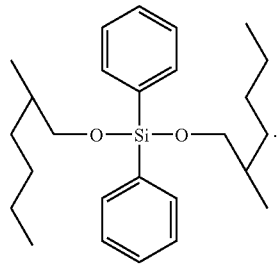
(6)

17. The liquid lens according to claim 16, wherein the insulating solution has a density of 1.0 g/cm$^3$ or more equal to that of an electrolyte solution, a refractive index of 1.5 $n_D^{20}$ or more greater than that of the electrolyte solution, and a viscosity of 10 mPa·s or less wherein the difference in viscosity between the insulating solution and the electrolyte solution is within 0.5 mPa·s.

18. A liquid lens module comprising:

a transparent cover;

a case for accommodating an electrolyte solution and an insulating solution;

a pair of electrodes for supplying electricity to the electrolyte solution; and an insulating film for covering one of the electrodes in contact with the electrolyte solution, wherein the insulating solution is the insulating composition according to claim 16.

19. The liquid lens according to claim 15, wherein the insulating solution has a density of 1.0 g/cm$^3$ or more equal to that of an electrolyte solution, a refractive index of 1.5 $n_D^{20}$ or more greater than that of the electrolyte solution, and a viscosity of 10 mPa·s or less wherein the difference in viscosity between the insulating solution and the electrolyte solution is within 0.5 mPa·s.

20. A liquid lens module comprising:

a transparent cover;

a case for accommodating an electrolyte solution and an insulating solution;

a pair of electrodes for supplying electricity to the electrolyte solution; and an insulating film for covering one of the electrodes in contact with the electrolyte solution, wherein the insulating solution is the insulating composition according to claim 15.

* * * * *

UNITED STATES PATENT AND TRADEMARK OFFICE
CERTIFICATE OF CORRECTION

PATENT NO. : 7,551,364 B2 Page 1 of 1
APPLICATION NO. : 11/706204
DATED : June 23, 2009
INVENTOR(S) : Jae Young Bae et al.

It is certified that error appears in the above-identified patent and that said Letters Patent is hereby corrected as shown below:

Title Page, Column 2 (Other Publications), item (56); Line 1, change "Enatiomeric" to --Enantiomeric--.

Column 8, Line 65, change "silicone oil" to --liquid lens--.

Column 8, Lines 65-66, change "liquid lens" to --silicone oil--.

Column 11, Line 36, change "10." to --12.--.

Column 13, Line 13, change "1 .5" to --1.5--.

Signed and Sealed this

Nineteenth Day of January, 2010

David J. Kappos
*Director of the United States Patent and Trademark Office*